United States Patent
Ershov et al.

(10) Patent No.: US 9,078,916 B2
(45) Date of Patent: Jul. 14, 2015

(54) METHOD FOR PRODUCING AND USING A COPOLYMER OF SODIUM CARBOXYMETHYL CELLULOSE AND GOSSYPOL

(75) Inventors: Felix Ivanovich Ershov, Moscow (RU); Vladimir Georgievich Nesterenko, Moscow (RU); Abdushukur Abdukhalilovich Sarymsakov, Tashkent (RU); Natalya Uryevna Alekseeva, Moscow (RU)

(73) Assignee: Limited Liability Company "Nearmedic Plus", Moscow (RU)

( * ) Notice: Subject to any disclaimer, the term of this patent is extended or adjusted under 35 U.S.C. 154(b) by 61 days.

(21) Appl. No.: 13/877,416

(22) PCT Filed: Oct. 6, 2011

(86) PCT No.: PCT/RU2011/000785
§ 371 (c)(1),
(2), (4) Date: Jun. 24, 2013

(87) PCT Pub. No.: WO2012/050483
PCT Pub. Date: Apr. 19, 2012

(65) Prior Publication Data
US 2013/0266534 A1   Oct. 10, 2013

(30) Foreign Application Priority Data
Oct. 11, 2010  (RU) .............................. 2010141697

(51) Int. Cl.
| | |
|---|---|
| A61K 31/765 | (2006.01) |
| A61K 31/717 | (2006.01) |
| A61K 45/06 | (2006.01) |
| C08B 11/12 | (2006.01) |

(Continued)

(52) U.S. Cl.
CPC ............ *A61K 31/765* (2013.01); *A61K 31/717* (2013.01); *A61K 45/06* (2013.01); *C08B 11/12* (2013.01); *C08B 15/00* (2013.01); *C08B 15/02* (2013.01)

(58) Field of Classification Search
CPC ..... A61K 9/20; A61K 31/717; A61K 31/765; A61K 31/775; A61K 45/02; C08B 11/12; C08B 15/00; C08B 15/02
USPC ........... 424/78.08, 78.38, 451, 464; 514/450, 514/451, 506, 511, 557, 569, 570; 560/56, 560/60, 75, 100; 562/405, 467, 475, 488, 562/489, 490; 527/303
See application file for complete search history.

(56) References Cited

U.S. PATENT DOCUMENTS

2009/0285865 A1 * 11/2009  Shalaby .................. 424/400

FOREIGN PATENT DOCUMENTS

RU        2002755 C1    11/1993
(Continued)

OTHER PUBLICATIONS

Emishanova, S.V., Avtoreferat dissertatsii na soikanie uchenoy stepeni doktora farmatsevticheskihk nauk. M., 2007 [on-line] [Found 2012-01-00] http://www.ceninauku.ru/page_19852.htm, p. 4, part 2.2.*

(Continued)

*Primary Examiner* — Jane C Oswecki
(74) *Attorney, Agent, or Firm* — Wolf, Greenfield & Sacks, P.C.; C. Hunter Baker; Xiaohong Shou

(57) ABSTRACT

The invention relates to the field of organic chemistry, pharmacology and medicine and concerns a method for producing a copolymer of sodium carboxymethyl cellulose and gossypol having the formula (I), as well as the use thereof in a combined treatment for patients with autistic spectrum disorders and cognitive impairment.

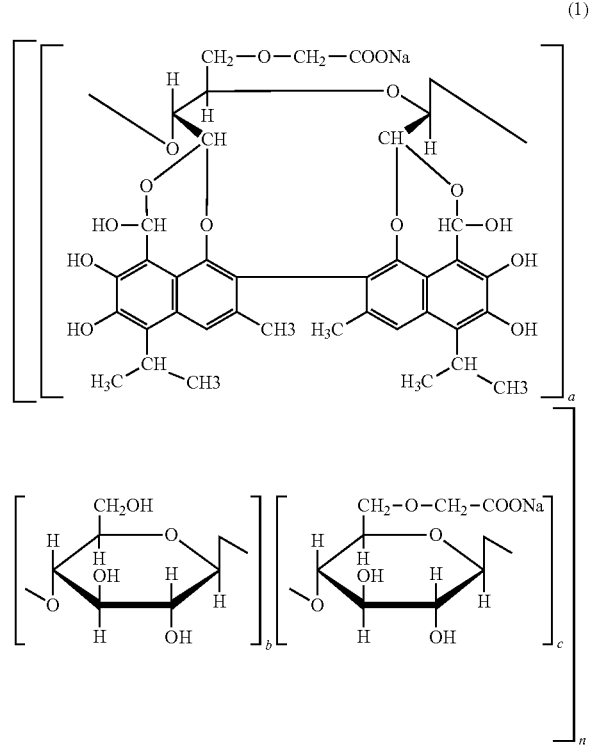

16 Claims, No Drawings

(51) Int. Cl.
*C08B 15/00* (2006.01)
*C08B 15/02* (2006.01)

(56) References Cited

FOREIGN PATENT DOCUMENTS

| RU | 2 222 548 C2 | 2/2004 | |
| RU | 2222548 C2 * | 2/2004 | ............... C08B 15/00 |
| RU | 2238122 C1 | 10/2004 | |
| RU | 2238122 C1 * | 10/2004 | ............... A61P 31/16 |
| RU | 2 270 708 C1 | 2/2006 | |
| RU | 2270708 C1 * | 2/2006 | ............... A61P 31/12 |
| RU | 2 324 476 C2 | 5/2008 | |

OTHER PUBLICATIONS

Emishanova S.V. Avtoreferat dissertatsii na soikanie uchenoy stepeni doktora farmatsevticheskihk nauk. M., 2007 [on-line] [Found Jan. 11, 2012] http://www.ceninauku.ru/page__19852.htm, p. 4, part 2.2.
International Preliminary Report on Patentability, mailed Apr. 25, 2013 for Application No. PCT/RU2011/000785.
International Search Report and Written Opinion, mailed Feb. 9, 2012 for Application No. PCT/RU2011/000785.

* cited by examiner

METHOD FOR PRODUCING AND USING A COPOLYMER OF SODIUM CARBOXYMETHYL CELLULOSE AND GOSSYPOL

RELATED APPLICATIONS

This application is a national stage filing under 35 U.S.C. §371 of international PCT application, PCT/RU2011/000785, filed Oct. 6, 2011, which claims priority to Russian patent application, no. 2010141697, filed Oct. 11, 2010, the entire contents of each of which are hereby incorporated by reference.

The invention relates to the field of organic chemistry, pharmacology and medicine and concerns a method for producing a copolymer of sodium carboxymethyl cellulose and gossypol, its use in complex therapy of patients with autistic spectrum disorders and cognitive impairments, as well as a pharmaceutical composition comprising thereof to be used in the treatment of patients with autistic spectrum disorders and cognitive impairments, a combination for the treatment of patients with autistic spectrum disorders and cognitive impairments and a method for treating such patients.

BACKGROUND

In recent decades, the aim of finding new agents for the treatment of autistic spectrum disorders accompanied by severe cognitive impairments becomes more medically and socially important in view of the duration of treatment, severe disability and maladjustment of patients with autistic spectrum disorders (V. M. Bashina, Childhood Autism, Moscow, "Meditsina", 1999).

Childhood autism is characterized by disorders of psychological development, autistic form of contact with others, disorders of speech and motor skills, activities and stereotyped behavior that lead to social maladjustment. A generally accepted concept of the etiology of autistic disorders does not currently exist. The reasons are different—from endogenous genetic to exogenous organic and psychogenic. Childhood autism is considered to have a neurobiological basis and to be a result of general brain disorders.

There are known medicaments for the treatment of autistic spectrum disorders accompanied by severe cognitive impairments, which include, first of all, neuroleptics. Among neuroleptics for the treatment of autistic disorders with severe cognitive impairments there are useful aminazine, neuleptil, haloperidol, teraligen, triphtazine, eglonil, azaleptin, chlorprothixene. In addition, such conditions are treated with antidepressants (anafranil, azaphene, pirazidole, amitriptyline, etc.), anticonvulsants (finlepsin, trileptal, topamax). (V. V. Kovalev, Psychiatry of childhood, Moscow, "Meditsin", 1979; V. M. Bashina, Childhood autism, Moscow, "Medicine", 1999).

It should be noted that the use of neuroleptics is accompanied by a high risk of undesirable side effects including extrapyramidal disorders, neuroleptic malignant syndrome, etc. A long-term treatment with such neuroleptics and other psychotropic agents results in evident side effects; they can cause psychological, neurological, and somato-vegetative disorders, which certainly limits the duration required for the neuroleptic therapy to be effective.

Sometimes, nootropics are used for the treatment of autistic disorders with severe cognitive impairments, as additional medicaments. Nootropics are considered to have a direct activating effect on learning, improving memory and mental activity, i.e. cognitive function. The most commonly used nootropics in the treatment of autistic disorders with severe cognitive impairments are glycine, nootropil (Pyracetam), encephabol (Pyriditol), aminalone (Gammalon), tanakan (L. M. Kuzenkova, O. I. Maslova, L. S. Namazova, etc., Nootropics in cognitive neuroscience in childhood//Manual for physicians, M., 2008, p. 54). Dose regimen of nootropics is adjusted individually. Although nootropics are basically characterized by good tolerability in children with severe intellectual maldevelopment, their administration can lead to increased motor disinhibition, irritability, hyperthymia, and sleep impairment. Nootropics are described to have other side effects: Piracetam can cause dyspeptic disorders and increased coronary insufficiency; aminalone can cause dyspeptic disorders, fever-sensation and changes in blood pressure; Pyriditol can cause nausea and headache, and in children—psychomotor agitation. With that, Pyracetam is contraindicated in renal failure; Pyriditol is contraindicated in high convulsion-readiness (L. M. Kuzenkova, O. I. Maslova, L. S. Namazova et al., Nootropics in cognitive neuroscience in childhood//Manual for physicians, M., 2008, p. 54; S. Yu. Shtrygol, T. V. Kortunova, D. V. Shtrygol, Side Effects of Nootropics, Provisor, 2003, Issue 11).

In addition, in recent years a complex therapy with the above indicated drugs is most effective for the treatment of autistic disorders with severe cognitive impairments. However, in this case, patients with very severe forms of autism often demonstrate resistance to neuroleptics, which requires increasing the average daily doses of medicaments. In this case, a desired effect is not always observed, and side effects are often increased.

In this context, the search for new additional agents for pathogenic therapy allowing for enhanced safety and efficacy of the treatment of mental illness is an important clinical and social challenge.

SUMMARY OF THE INVENTION

The present inventors have surprisingly found that a known sodium salt of copolymer of carboxymethyl cellulose with a degree of substitution of 0.35 to 0.80 and gossypol, of formula (1):

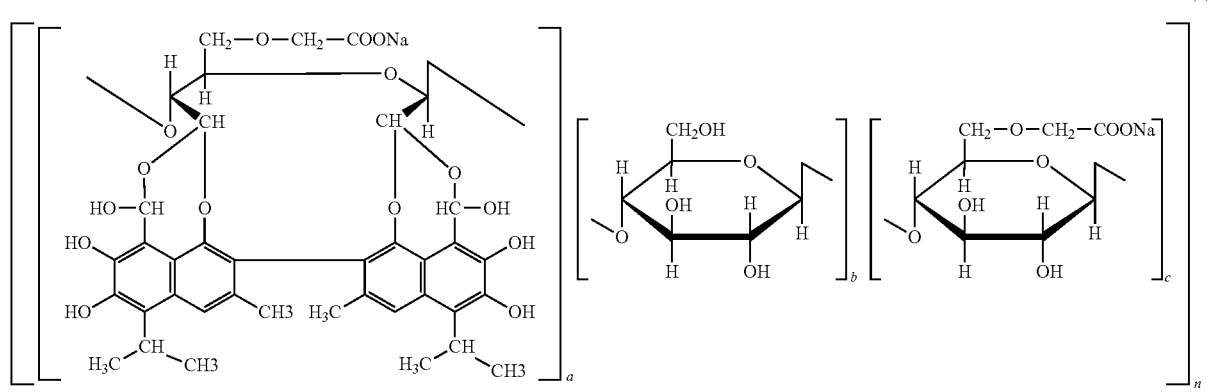

(1)

where
a:b:c=1:(3-6):(5-7),
n=40-50;
with a molecular weight of 120,000-130,000, and
of the following empirical formula:

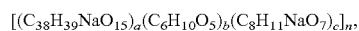

wherein the sodium salt has antiviral activity and is used for the treatment of various viral infections, can be successfully used to treat patients with autistic spectrum disorders and cognitive impairments.

The compound and the method for producing thereof are described in RU 2270708. According to the known method an aqueous solution of sodium carboxymethyl cellulose is reacted with an aqueous solution of periodic acid or sodium periodate in the presence of isopropyl alcohol, followed by washing the resulting dialdehyde carboxymethyl cellulose with a mixture of isopropyl alcohol and water acidified with hydrochloric acid, treating with gossypol or gossypol-acetic acid and then with an aqueous solution of sodium hydroxide, and isolating the desired product by precipitation of a solvent.

The product obtained by the known method is contaminated with hydrochloric acid and isopropyl alcohol. In addition, operations involving hydrochloric acid solutions are always associated with certain difficulties.

Therefore, the object of the present invention is to develop an improved method for producing a copolymer of carboxymethyl cellulose with a degree of substitution of 0.35 to 0.80 and gossypol, of formula (I) without the above indicated drawbacks.

Thus, an aspect of the present invention is a method for producing a copolymer of sodium carboxymethyl cellulose with a degree of substitution of 0.35 to 0.80 and gossypol, of the above formula (I), with a molecular weight of 120,000 to 130,000, wherein the method comprises reacting an aqueous solution of sodium carboxymethyl cellulose with a degree of substitution of 0.35 to 0.80 with an aqueous solution of periodic acid or sodium periodate when carbon dioxide is passed through the reaction solution until reaching a pH of 3.0 to 4.5, followed by isolation of dialdehyde carboxymethyl cellulose, treatment of the obtained product with gossypol or gossypol-acetic acid and then with an aqueous alkaline solution, and isolation of the desired product by precipitation with an organic solvent.

In order to isolate dialdehyde carboxymethyl cellulose, the reaction mixture, after reaching a pH of 3.0 to 4.5, is incubated at 5-8° C. in a light-protected place for from 15 to 18 hours; the obtained dialdehyde carboxymethyl cellulose is precipitated with acetone and washed with an organic solvent, preferably with 70% aqueous acetone and 80% aqueous alcohol. Further treatment with gossypol or gossypol-acetic acid is performed at a temperature of 18 to 20° C., followed by neutralization of the reaction mixture with an alkaline solution and isolation of the desired product by precipitation with an organic solvent, preferably with acetone.

The proposed method excludes processes involving isopropyl alcohol and hydrochloric acid solutions, and provides a high yield of the desired product.

Another aspect of the present invention is a use of a copolymer of sodium carboxymethyl cellulose with a degree of substitution of 0.35 to 0.80 and gossypol, of the above formula (I) in complex therapy of patients with autistic spectrum disorders and cognitive impairments. In particular, said polymer is used in combination with a medicament used for the treatment of cognitive disorders, which are selected from one or more neuroleptics, antidepressants, anticonvulsants, or a combination thereof. It is most preferable to use said polymer produced by the method according to the present invention.

Another aspect of the present invention is a pharmaceutical composition for the treatment of patients with autistic spectrum disorders and cognitive impairments, comprising, as an active agent, a therapeutically effective amount of a copolymer of sodium carboxymethyl cellulose with a degree of substitution of 0.35 to 0.80 and gossypol, of the above formula (I), and pharmaceutically acceptable additives.

The proposed pharmaceutical composition can be prepared in various formulations depending on the method of using thereof. An oral pharmaceutical composition can be used in the form of tablets, capsules or suspensions. In addition, suppositories can be used for rectal administration. The amount of an active agent in a pharmaceutical composition can vary within a wide range depending on various factors well known in the pharmaceutical field. As pharmaceutically acceptable additives, substances generally used for the above formulations can be used. For example, starch, such as potato starch, calcium or magnesium stearate, lactose, and other pharmaceutically acceptable additives can be used as an excipient in tablets.

Currently, the problem of reducing the amount of allergenic agents in pharmaceutical preparations acquires more importance. In this regard, the use of ludipress comprising direct-compression lactose, povidone, pyrrolidone and crospovidone as a pharmaceutically acceptable additive allows complete replacement of lactose in pharmaceutical preparations and reduction of the amount of such allergenic agents such as starch, and reduction of the amount of calcium or magnesium stearate, increasing thereby the strength of tablets.

In this regard, in a preferred embodiment the proposed pharmaceutical composition can have the following ratio of the components, in wt. %:
active agent of the above formula (I)—10.0-16.0
starch—10.0-20.0
calcium or magnesium stearate—0.6-0.8
ludipress—up to 100.

The pharmaceutical composition of the present invention is generally used in combination with a medicament used for the treatment of cognitive disorders, which is selected from one or more neuroleptics, antidepressants, anticonvulsants, or a combination thereof.

Thus, another aspect of the present invention is a combination for the treatment of patients with autistic spectrum disorders and cognitive impairments, comprising a therapeutically effective amount of a copolymer of sodium carboxymethyl cellulose with a degree of substitution of 0.35 to 0.80 and gossypol, of the above formula (I) or a pharmaceutical composition comprising thereof; and a therapeutically effective amount of a medicament used for the treatment of cognitive disorders, which is selected from one or more neuroleptics, antidepressants, anticonvulsants or a combination thereof.

Accordingly, another aspect of the present invention is a method of treating patients with autistic spectrum disorders and cognitive impairments, comprising administering to a patient a therapeutically effective amount of a copolymer of sodium carboxymethyl cellulose with a degree of substitution of 0.35 to 0.80 and gossypol, of the above formula (I) in combination with a therapeutically effective amount of a medicament used for the treatment of cognitive disorders, which is selected from one or more neuroleptics, antidepressants, anticonvulsants, or a combination thereof.

The method can be used for the treatment of autistic disorders and cognitive impairments in 6-year children. A treatment regimen is selected by a specialist depending on the severity of a disease, condition and age of a patient. In particular, the treatment can be performed according to the following regimen: administration of a medicament 3 times per day for 5 days followed by the 5-day break. This ten-day cycle is repeated 2 times. The total duration of the treatment is 30 days. A dose of the active agent is 36 mg/day. Then, the course should be repeated.

A medicament used for the treatment of cognitive disorders is selected from neuroleptics, antidepressants and anticonvulsants. Aminazine, neuleptil, haloperidol, teraligen, triphtazine, eglonil, azaleptin, and chlorprothixene are used as commonly used neuroleptics. Medicaments such as anafranil, azaphene, pirazidole, and amitriptyline can be used as antidepressants. Finlepsin, trileptal, and topamax are commonly used as anticonvulsants.

Examples of producing a copolymer of sodium carboxymethyl cellulose with a degree of substitution of 0.35 to 0.80 and gossypol, of formula (I) and examples of pharmaceutical compositions comprising the copolymer and a method of treating are provided below.

EXAMPLE OF PRODUCTION 1-8

Procedure: A 3% aqueous solution is prepared from 100 g of sodium carboxymethyl cellulose (Na-CMC) with a degree of substitution of 0.35 in a reactor equipped with a mechanical stirrer. A 1% aqueous solution of periodic acid or sodium periodate in an amount of 1600 ml was added to the obtained Na-CMC solution. After complete mixing, gaseous carbon dioxide is passed through the solution until reaching a pH value of the solution of 3.0 to 4.5. Then, the reaction mixture is incubated at a temperature of 5 to 8° C. for 15-18 hours. The reaction product is precipitated and washed with 70% acetone and 80% aqueous alcohol solution from the excess of the oxidant and the products of degradation thereof. Gossypol (or gossypol-acetic acid) in an amount of 15% of the initial mass of sodium carboxymethyl cellulose is added to the washed product, which is dialdehyde carboxymethyl cellulose, and stirred at 18-20° C. for 5 minutes. The reaction mixture is neutralized with a 6% aqueous solution of sodium hydroxide to a pH factor of 9.0. The desired product is isolated by precipitation with acetone followed by washing with the same solvent to complete removal of the excess of gossypol or its adduct, and drying on air. The yield of the desired product is 88%.

Specific data of examples 1-8 of the production of the claimed compound are shown in Table 1.

TABLE 1

Examples of the production of the claimed compound

| Examples of the method embodiments | Degree of substitution of initial Na CMC | Concentration of aqueous Na CMC, % | Concentration of periodic acid or a salt thereof, % | Volume of a solution of periodic acid or a salt thereof, % | pH of the solution in oxidation of Na CMC | Temperature of incubation, ° C. | Time of incubation of the solution during oxidation, hours | Amount of gossypol or its adduct taken for a reaction, % |
|---|---|---|---|---|---|---|---|---|
| 1 | 0.35 | 3 | 1 | 1600 | 3.0 | 5 | 18 | 15.0 |
| 2 | 0.50 | 5 | 2 | 700 | 3.5 | 7 | 16 | 10.0 |
| 3 | 0.65 | 7 | 4 | 300 | 4.0 | 8 | 15 | 7.5 |
| 4 | 0.80 | 10 | 6 | 170 | 4.5 | 5 | 15 | 5.0 |
| 5 | 0.35 | 5 | 2 | 700 | 3.5 | 8 | 18 | 10.0 |
| 6 | 0.50 | 3 | 1 | 1600 | 3.0 | 6 | 16 | 15.0 |
| 7 | 0.65 | 10 | 6 | 170 | 4.5 | 7 | 16 | 5.0 |
| 8 | 0.80 | 7 | 4 | 300 | 4.0 | 5 | 15 | 7.5 |

TABLE 1-continued

Examples of the production of the claimed compound

| Examples of the method embodiments | Temperature in mixing gossypol or its adduct, °C. | Time of mixing dialdehyde, sec | pH of reaction mass in mixing in an alkaline solution | Characteristic viscosity, g | Molecular weight of the product | Water solubility, % | Yield of the desired product, % |
|---|---|---|---|---|---|---|---|
| 1 | 20 | 5.0 | 10.5 | 0.21 | 36300 | 99.0 | 95 |
| 2 | 22 | 4.0 | 10.0 | 0.19 | 30000 | 99.3 | 94 |
| 3 | 23 | 3.0 | 10.0 | 0.18 | 29100 | 99.6 | 93 |
| 4 | 25 | 3.0 | 10.5 | 0.12 | 24300 | 99.8 | 92 |
| 5 | 22 | 4.0 | 10.0 | 0.20 | 35400 | 99.1 | 94 |
| 6 | 20 | 5.0 | 10.5 | 0.19 | 31300 | 99.4 | 93 |
| 7 | 25 | 3.0 | 10.5 | 0.17 | 30800 | 99.5 | 91 |
| 8 | 23 | 3.0 | 10.0 | 0.13 | 25100 | 99.7 | 92 |

Example of Formulation 1

Tablets

Tablets were produced by a conventional method, in particular, by mixing components and pressing on a tableting machine. Examples of the quantitative composition of a tablet are shown in Table 2.

TABLE 2

Examples of the quantitative composition of a tablet

| | No of example | | | | | |
|---|---|---|---|---|---|---|
| | 1 | | 2 | | 3 | |
| | Tablet weight | | | | | |
| | 100 mg | | 150 mg | | 200 mg | |
| Components | Amount, mg | % | Amount, mg | % | Amount, mg | % |
| Active agent(*) | 12 | 12 | 18 | 12 | 24 | 12 |
| Potato starch | 10 | 10 | 15 | 10 | 20 | 10 |
| Calcium stearate | 0.65 | 0.65 | 0.98 | 0.65 | 1.30 | 0.65 |
| Ludipress | 77.35 | 77.35 | 116.02 | 77.35 | 154.70 | 77.35 |

(*)copolymer of sodium carboxymethyl cellulose with a degree of substitution of 0.35 to 0.80 and gossypol, of formula (I).

The solubility test has demonstrated that 100% of the active agent transfers to the solution when dissolving a tablet in 500 ml of water on a mixer at 100 rpm for 45 minutes.

Treatment of 6-Year Children with Autistic Spectrum Disorders and Severe Cognitive Impairments The efficacy and safety of the use of sodium carboxymethyl cellulose polymer with a degree of substitution of 0.35 to 0.80 and gossypol, of formula (I) in a complex therapy of 6-year children with autistic spectrum disorders and severe cognitive impairments were studied. The children were administered with a medicament comprising a copolymer of sodium carboxymethyl cellulose with a degree of substitution of 0.35 to 0.80 and gossypol, of formula (I) (tablets containing 12 mg of the active agent, which composition is shown in Table 2) on the background of basic therapy with neuroleptics such as neuleptil, haloperidol, aminazine, teraligen, triphtazine, eglonil, azaleptin chlorprothixene. Antidepressants (e.g., anafranil) and anticonvulsants (finlepsin, trileptal, or topamax) were used in some cases. Neuroleptics, antidepressants and anticonvulsants were used in optimal therapeutic doses. The group of patients administered, additionally to the basic therapy, with a medicament comprising a copolymer of sodium carboxymethyl cellulose with a degree of substitution of 0.35 to 0.80 and gossypol, of formula (I) demonstrated a decreased resistance to therapy with neuroleptics, especially the patients with very severe autism. Before the administration of a medicament comprising a copolymer of sodium carboxymethyl cellulose with a degree of substitution of 0.35 to 0.80 and gossypol, of formula (I), these patients did not demonstrate a positive therapeutic effect in increasing doses of neuroleptics, and in some cases, complications of the conducted therapy were amplified to the loss of neatness skills (encopresis, enuresis). When the therapy was supplemented with a medicament comprising a copolymer of sodium carboxymethyl cellulose with a degree of substitution of 0.35 to 0.80 and gossypol, of formula (I), the manifestations of encopresis and enuresis ceased, catatonic disorders decreased, cognitive functions improved, and speech appeared. In patients with mild to moderate autism, restricted repetitive behavior disappeared.

The mental condition of the patients is improved when administering a medicament comprising a copolymer of sodium carboxymethyl cellulose with a degree of substitution of 0.35 to 0.80 and gossypol, of formula (I). The use of sodium carboxymethyl cellulose polymer with a degree of substitution of 0.35 to 0.80 and gossypol, of formula (I) as a component of complex therapy of children with autistic spectrum disorders and severe cognitive impairments allows elimination of the body's resistance to psychotropic drugs, thereby achieving a therapeutic effect with decreased single and daily doses of the medicaments for basic therapy, and a significant improvement in cognitive functions of patients. The use of a medicament comprising a copolymer of sodium carboxymethyl cellulose with a degree of substitution of 0.35 to 0.80 and gossypol, of formula (I) does not have negative side effects on a patient. The medicament is well tolerable; toxic and allergic reactions were not reported.

Thus, the present invention allows the production of a copolymer of sodium carboxymethyl cellulose with a degree of substitution of 0.35 to 0.80 and gossypol, of formula (I) by a safe work method providing a high yield of the desirable product and allows an effective use of said product in complex therapy of patients with autistic spectrum disorders and cognitive impairments.

The invention claimed is:

1. A method of preparing a copolymer of sodium carboxymethyl cellulose with a degree of substitution of 0.35 to 0.80 and gossypol, wherein the copolymer is of Formula (1):

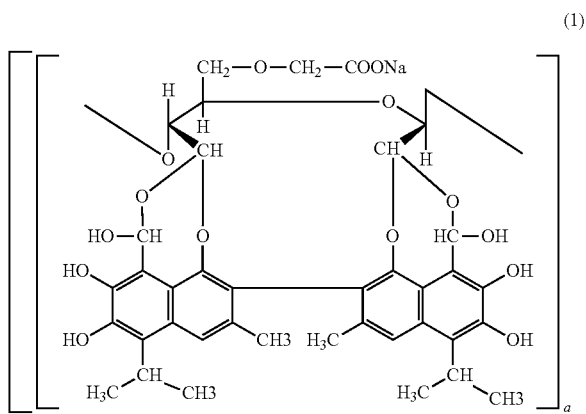

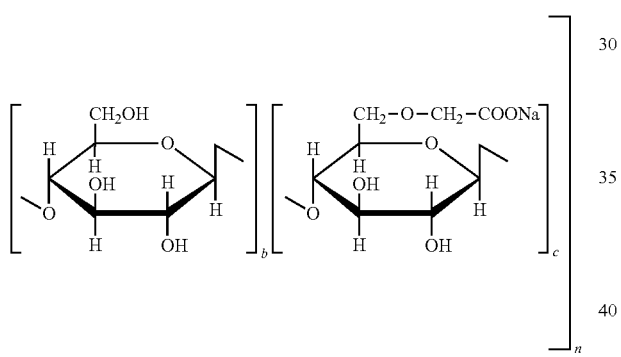

wherein
a:b:c is 1:(3-6):(5-7);
n is 40-50; and
the copolymer has a molecular weight of 120,000-130,000;
comprising
(a) reacting an aqueous solution of sodium carboxymethyl cellulose with a degree of substitution of 0.35 to 0.80 with an aqueous solution of periodic acid or sodium to form a reaction mixture, wherein the reaction mixture reaches a pH value of 3.0 to 4.5 when carbon dioxide is passed through the reaction mixture; then incubating the reaction mixture at 5-8° C. in a light-protected place for from 15 to 18 hours;
(b) isolating crude dialdehyde carboxymethyl cellulose from the reaction mixture of step (a);
(c) treating the crude dialdehyde carboxymethyl cellulose with gossypol or gossypol-acetic acid to form another reaction mixture;
(d) neutralizing the reaction mixture of step (c) with an aqueous alkaline solution; and
(e) isolating the copolymer by precipitation with an organic solvent.

2. The method of claim 1, wherein crude dialdehyde carboxymethyl cellulose is washed with acetone and an aqueous alcohol solution before treated with gossypol or gossypol-acetic acid.

3. The method of claim 1, wherein the copolymer is precipitated with acetone.

4. A pharmaceutical composition comprising
a therapeutically effective amount of a copolymer of sodium carboxymethyl cellulose with a degree of substitution of 0.35 to 0.80 and gossypol, pharmaceutically acceptable additives, and one or more neuroleptics, antidepressants, anticonvulsants, or a combination thereof, wherein the copolymer is of Formula (1):

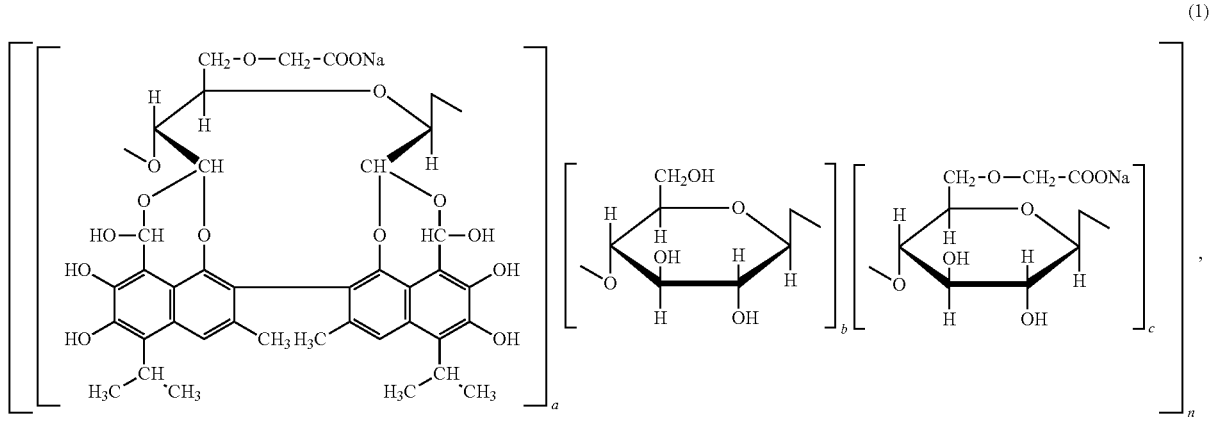

wherein
a:b:c is 1:(3-6):(5-7);
n is 40-50; and
the copolymer has a molecular weight of 120,000-130,000.

5. The pharmaceutical composition according to claim 4, wherein:
the copolymer is 10.0-16.0 wt %;
starch is 10.0-20.0 wt %;
calcium or magnesium stearate is 0.6-0.8 wt %; and
ludipress is up to 100 wt %.

6. The pharmaceutical composition according to claim 4 in the form of a tablet, capsule, or suspension.

7. A method for treating a patient with an autistic disorder or cognitive impairment comprising administering to a patient suffering from an autistic disorder or cognitive impairment a therapeutically effective amount of a copolymer of sodium carboxymethyl cellulose with a degree of substitution of 0.35 to 0.80 and gossypol, or a pharmaceutical composition comprising the copolymer and pharmaceutically acceptable additives, wherein the copolymer is of Formula (1):

8. The method of claim 7, wherein the neuroleptic is selected from the group consisting of aminazine, neuleptil, haloperidol, teraligen, triphtazine, eglonil, azaleptin, and chlorprothixene.

9. The method of claim 7, wherein the antidepressant is selected from the group consisting of anafranil, azaphene, pirazidole, and amitriptyline.

10. The method of claim 7, wherein the anticonvulsant is selected from the group consisting of finlepsin, trileptal, and Topamax.

11. The method of claim 7, wherein the step of administering comprises administering the copolymer orally or rectally.

12. The method of claim 7, wherein the step of administering is performed three times a day for five days, followed by a five-day break.

13. The method of claim 12, wherein the step of administering is further performed three times a day for five days, followed by a five-day break.

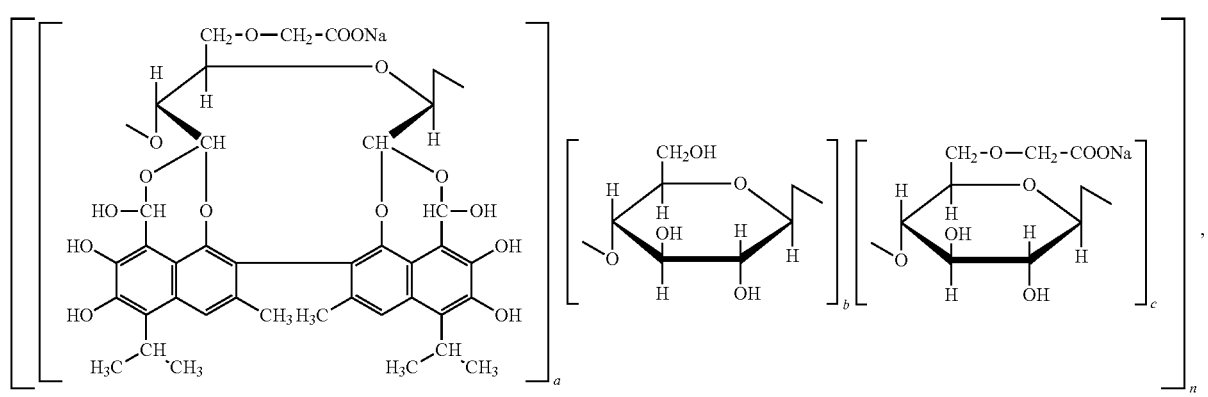

wherein
a:b:c is 1:(3-6):(5-7);
n is 40-50; and
the copolymer has a molecular weight of 120,000-130,000;
and a therapeutically effective amount of one or more neuroleptics, antidepressants, anticonvulsants, or a combination thereof.

14. The method of claim 7, wherein the copolymer is administered at a dose of approximately 36 mg per day.

15. The method of claim 7, wherein the patient is a child.

16. The method of claim 1, wherein step (c) is carried out at a temperature of 18 to 20° C.

* * * * *